United States Patent [19]

James et al.

[11] Patent Number: 4,656,033
[45] Date of Patent: Apr. 7, 1987

[54] ISOLATED, SOLUBLE IMMUNOGEN AGAINST *SCHISTOSOMA MANSONI* AND A METHOD OF VACCINATION EMPLOYING SAME

[75] Inventors: Stephanie L. James; Alan Sher, both of Rockville, Md.

[73] Assignee: The United States of America as represented by the Department of Health and Human Services, Washington, D.C.

[21] Appl. No.: 741,600

[22] Filed: Jun. 5, 1985

[51] Int. Cl.$^4$ .................................... A61K 39/062
[52] U.S. Cl. .................................... 424/88
[58] Field of Search .................................... 424/88, 92

[56] References Cited

U.S. PATENT DOCUMENTS 4,158,049  6/1979  Pelley et al. .................. 424/88
4,396,600  8/1983  Messineo et al. .............. 424/88

OTHER PUBLICATIONS

Olds C.A.93 #61512k (1980); Khayyal C.A.93 #61634b (1980).
Boros C.A.78 #109163s (1973); Zwisler C.A.88 #168419j (1978).
Pelley C.A.87 #100328c (1977); Tribouley C.A.87 #51470g (1977).
James et al. C.A.103 #4691u (1985); Bawden C.A.82 #55465d (1975).
Auriault C.A.100 #190028u (1984); Khayyal C.A.80 #44032t (1974).
Horowitz C.A.97 #4525a (1982); Khayyal C.A.68 #48157n (1968).
Byram C.A.95 #130836z (1981).
Tribouley C.A.93 #68446a (1980).
James, Journ. of Immun. 134:1956-60 (1985).
James, et al., Journ. of Immun. 134:3432-38 (1985).
Horowitz, et al., Eur. J. Immun. 12:327-32 (1982).
Hillyer, Supp. Parasitology, 48:287-95 (1979).
Civil, et al., (1978).
James, et al., Cullular Immun. 65:75-83 (1981).
Deelder, et al., Am. J. Trop. Med. Hyg. pp. 401-10 (1980).
Kirchhoff, et al., Journ. of Immun. 133:2731-35 (1984).
Colley, et al., Int. Archs Allergy Appl. Immun. 53:420-433 (1977).

*Primary Examiner*—Shep K. Rose
*Attorney, Agent, or Firm*—Holman & Stern

[57] ABSTRACT

The present invention discloses a method of vaccination against *Schistosoma mansoni* employing membrane-free, soluble immunogens. It has been found that the route of administering the vaccine and fortification thereof with a suitable adjuvant are quite critical in eliciting immunity in the host.

3 Claims, 5 Drawing Figures

ISOLATED, SOLUBLE IMMUNOGEN AGAINST *SCHISTOSOMA MANSONI* AND A METHOD OF VACCINATION EMPLOYING SAME

The present invention was conducted in part by a NIH grant #AI21082 to Stephanie L. James.

BACKGOUND OF THE INVENTION

1. Technical Field

The present invention is related to an isolated, soluble parasite fraction capable of providing protective immunization against *Schistosoma mansoni* (*S. mansoni*) parasitic infection. More particularly, the present invention is related to a method of inducing protective immunity against *Schistosoma mansoni* in a host by intradermally administering to said host soluble parasite antigens combined with a suitable adjuvant.

2. Prior Art:

Immunologically based resistance to schistosomiasis can be induced in experimental animals by prior exposure to living-infective or radiation-attenuated parasites. Such observations indicate that this helminthic disease, which afflicts millions of people as well as domestic animals in parts of South America, Africa and Asia, could be controlled by vaccination. However, it is quite apparent that irradiated parasites, which have been successfully employed for vaccination of cattle in fields trials, would be unreliable and inefficient for widespread use or for immunization in man. Clearly, production of a defined vaccine would be more desirable. Yet, efforts to induce immunity with non-living schistosome preparations have been almost entirely unsuccessful. Two reported exceptions, involving immunization with alum-adsorbed cercarial sonicate (Horowitz et al. Eur. J. Immunol. 12:327) and cross-reacting *Fasciola hepatica* preparations (Hillyer. Exp. Parasitol. 48:287) require multiple immunizations and use of harsh adjuvants, making the procedures undesirable for potential use in humans.

SUMMARY

It is, therefore, an object of the present invention to provide an isolated, non-membranous, soluble antigen or fraction thereof from *Schistosoma mansoni* capable of inducing protective immunity against schistosomiasis.

It is a further object of the present invention to provide a method of protecting a host against schistosomiasis by intradermally administering to said host an immunogenic amount of a non-membranous, antigen from *Schistosoma mansoni*.

It is a still further object of the present invention to fortify said protein with a suitable adjuvant to induce increased immunogenic response in the host.

It is yet another object of the present invention to provide a pharmaceutical preparation for controlling or preventing schistosomiasis in mammals comprising the antigen of the present invention in a sterile, pharmaceutically acceptable carrier or adjuvant for administration to a host in an amount suitable for inducing protective immunity against schistosomiasis in said host.

Other objects and advantages of the present invention will become apparent as the detailed description of the invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows results of immunization against *S. mansoni* using dead invasive larvae. Groups of 10 C57BL/6J mice were treated by one intradermal/subcutaneous (id) injection of 0.1 ml phosphate-buffered saline containing dead schistosomula of *S. mansoni* prepared by one cycle of freezing at $-20°$ C. and thawing (FT). Alternatively, dead larvae were injected intravenously (iv) in 0.5 ml of saline. *Mycobacterium bovis*, strain BCG was included at $5 \times 10^6$ CFU/injection. Mice vaccinated by percutaneous exposure to 500 radiation-attenuated (50 Kr) cercariae served as positive controls in two experiments. Unimmunized animals served as negative controls in each experiment. Mice were infected with *S. mansoni* cercariae at 4 weeks after immunization. Percent resistance to infection conferred by immunization was calculated by perfusion of adult worms from the portal system at 6 weeks after infection, comparing numbers recovered from immunized groups to those recovered from unimmunized groups in each experiment. Results are expressed as mean percent resistance ±standard error (SE) for the number of experiments stated in parentheses.

DETAILED DESCRIPTION OF INVENTION

The above objects and advantages of the present invention are achieved by a membrane-free, soluble antigen preparation capable of inducing in a mammalian host protective immunity against schistosomiasis or *S. mansoni* induced disease.

Although any suitable or equivalent materials and methods can be employed in the practice of the present invention, the following materials and methods are preferred. All publications mentioned hereunder are incorporated herein by reference.

Animals and Parasites.

Female C57BL/6J mice were obtained from Jackson Laboratories (Bar Harbor, ME) at 6 to 8 weeks of age. *S. Mansoni* cercariae (NMRI strain) were obtained from infected Biomphalaria glabrata snails purchased from the Biomedical Research Institute (Rockville MD).

Antigens and Immunization.

Mice were divided into groups of 10 animals each. Antigen was prepared by mechanical transformation of cercariae to schistosomula and purification over a density gradient (Lazdines, et al. Exp. Parasitol. 53:39, 1982). After 3 hours of incubation, larvae were washed, counted, concentrated and frozen at $-20°$ C. At the time of immunization, the lysed larvae were resuspended at $10^5$/ml in sterile phosphate-buffered saline (PBS). The preparation therefore contained both soluble and particulate components of the parasites. Frozen and thawed (FT) larvae were injected intradermally/-subcutaneously (id) at $10^4$ schistosomula in 0.1 ml physiological, sterile saline. *Myobacterium bovis*, strain BCG, Phipps substrain (Trudeau Institute, Saranac Lake, NY) was included in the id inocula at $5 \times 10^6$ colony forming units (CFU)/injection. In some tests, FT-larval lysate was separated into soluble and particulate portions. Resuspended larvae were centrifuged for 5 minutes at $12,000 \times G$ in a Microfuge B (Beckman Instruments, Fullerton, CA). Supernatant fluid was used directly for immunization. Pelleted material was washed 3 times in PBS and resuspended at the original volume for injection. Alternatively, FT-larvae ($10^5$/ml) were sonicated for 15 seconds and centrifuged at $100,000 \times G$ for 1 hour. The resultant soluble schistosomulum antigen preparation (SCHLAP) remaining as supernate was standardized according to protein content (Lowry, et al. J. Biol. Chem. 193:265, 1951) at approximately 1.6 mg/ml. Soluble adult worm antigenic preparation (SWAP) was prepared by ultracentrifugation of homogenized male and female worms and protein content determined (Colley et al. Int. Arch. Allergy. Appl. Immunol. 53:420, 1977). These preparations routinely contained 10 to 11 mg of protein/ml. Soluble antigens were mixed with BCG and utilized at 0.1 ml volumes for immunization. Unimmunized animals, receiving only saline or BCG in saline, served as negative controls. Mice vaccinated by percutaneous exposure to 500 gamma-irradiated cercariae served as positive controls.

Infection and Determination of Resistance.

Four weeks after immunization, mice were infected with 150 to 200 *S. mansoni* cercariae by exposure of the abdominal skin on a site at least 2 cm from the id immunization site. Percent resistance was calculated by perfusion of adult worms from the portal vein at 6 weeks after infection, comparing numbers recovered from immunized groups to those recovered from unimmunized control groups in each experiment.

Assays for Antibody Production.

Two to three days prior to infection, serum samples were collected by bleeding the mice from the tail veins. Pooled sera from all animals in each group were analyzed for circulating antibodies to schistosomulum surface antigens by indirect immunofluorescence as described by Correa-Oliveria et al. (J. Immunol. 133:1581, 1984). Living mechanically transformed schistosomula or 2 week and 6 week liver stage worms were incubated in 1:2 dilutions of sera from immunized or control mice, washed and incubated with a 1:40 dilution of flourescein- conjugated goat antimouse IgG heavy and light chain antisera (reactive with IgG, IGM and IgA) (Cappel Laboratories, Malvern, PA). After washing, bound fluorescence was quantitated using a fluorescence microscope equipped with a Leitz MPV photometer. For each sample, readings were made on 15 to 20 individual larvae or 5 to 10 liver stage worms. Sera from all groups within an experiment were assayed at the same time. Results are presented as mean fluorescence in relative units (RFU) $\pm$SD for multiple experiments). Single dilution assays have been found to provide a good approximation of relative antibody levels obtained in titration experiments. (James et al. Cell Immun 65:75, 1981).

Production of antibodies to other constituents of schistosomula and adult worms was measued by ELISA using a modification of the procedure of Deelder et al. Am. J. Trop. Med. Hyg. 29:401, 1980 . Soluble parasite antigens were diluted in 0.06M, pH 9.5 carbonate buffer. Optimal concentrations of 10 $\mu$g/ml SWAP and 100 $\mu$g/ml SCHLAP were determined by titration using positive sera from vaccinated or chronically infected mice. Microtiter plates (Immulon I, Dynatech Laboratories, Alexandria, VA) were sensitized with 0.1 ml of antigen solution per well. Binding sites were then blocked by incubation with PBS—0.05% Tween 20 containing 0.5% bovine serum albumin (BSA). Sera were tested at dilutions of 1:15 to 1:1000 in PBS-Tween 20 buffer. Peroxidase-conjugated rabbit anti-mouse IgG heavy and light chain antisera was used at a 1:500 dilution (Cappel). 2.2'-azino-di [3-ethylbenzthiazoline sulfonate]served as substrate (Kirkiegaard and Perry Laboratories, Gaithersburg, MD). The reaction was stopped by addition of 50 $\mu$l of 0.5% sodium dodecyl sulfate to each well. Reactions were measured at 410 nm on a Micro-ELISA minireader MR590 (Dynatech). Results are presented as mean specific reactivity in optical density units (O.D. 410 $\pm$S.D.). Titer endpoints were taken as the last dilution giving a reading greater than 3 S.D. from the mean value of control sera.

Immunochemical Analyses.

The molecular weights of schistomulum surface antigens recognized by sera from immunized mice were determined by immunoprecipitation of $^{125}$I-labelled larvae. Three hour mechanically transformed schistosomula were washed in PBS at 4° C. and surface labelled using the Iodogen method. Briefly, 100 $\mu$g of Iodogen (1,3,4,6 tetrachloro -3 $\alpha$, 6 $\alpha$diphenyl glycoluril) (Pierce Chemical Co., Rockford, IL) were dissolved in 500 $\mu$l chloroform and evenly dispersed in the bottom of a glass scintillation vial by evaporation of the solvent under nitrogen. Approximately 50,000 larvae in 500 $\mu$l of PBS were mixed with 200 $\mu$Ci of Na$^{125}$I (Amersham, Arlington Heights, IL) and introduced into the Iodogen coated vial. After 7 minutes of gentle agitation on ice, the larvae were removed and washed in PBS containing 1% BSA. Parasites were intact and motile after this treatment. The $^{125}$I-labelled schistosomula were then resuspended in 500 $\mu$l of lysis buffer containing 2% NP 40, 0.5% deoxycholate, 10 mM Tris (pH 8.2) and 0.15 mM NaCl, as well as the protease inhibitors 1.6 mM phenyl methylsulfonyl fluoride, 2.8 KIU/ml aprotinin, 1 mM tosyl - L - lysine chloromethyl ketone and 10 μl/ml L-1-tosylamide -2-phenyl ethylchloromethyl ketone (Sigma Chemical Co., St. Louis, MO). Antigen extraction proceeded for 4 hours at 4° C. with frequent mixing. Pelletable material remaining after microcentrifugation (5 minutes at 4° C.) was discarded, and the supernatant was used as the antigen source. Ninety to 100% of the available counts were extracted by this method. Immunoprecipitation of labelled antigens was carried out as described by Kirchkoff, et al. J. Immunol. 133:2371, 1984, using serum dilutions of 1:10 and protein A- Sepharose (Pharmacia Fine Chemical, Piscataway, N.J.). Samples were separated by electrophoresis and autoradiographed.

For Western blot analysis, 3 hour schistosomula were solubilized by boiling for 5 minutes in 1% sodium dodecyl sulfate (SDS), 50 mM Tris (pH 8.0), 2.5% β-mercaptoethanol and 1 mM phenyl methyl sulfonyl flouoride. Solubilized antigens remaining in the supernatant fluid after microcentrifugation were used as total larval preparation. The SWAP used for Western blotting was equivalent to that used for immunization. Electrophoresis buffer (1.25% SDS, 60 mM Tris-HCl pH 6.8, 1.3% β-mercaptoethanol and 8% glycerol) was added to SWAP at a ratio of 2:1 and the mixture boiled 3 minutes.

Samples were separated by SDS-polyacrylamide gel electrophoresis (SDS-PAGE), using 7.5 to 15% gradient slab gels. For Western blotting, proteins were transferred from the gel to nitro cellulose paper. After blotting, the paper was quenched in PBS containing 0.05% Tween-20 and 10% fetal bovine sera (Hyclone Sterile Systems, Logan UT) (T-PBS +10% FBS) for 1 hour at 38° C. The paper strips were then reacted with antisera, at a 1:300 dilution, in T-PBS+5% FBS for 2 hours at room temperature. The strips were subsequently washed×6 in T-PBS+1% FBS and overlaid with $^{125}$I-labelled protein A (ICN, Irvine, Calif.) at approximately $5 \times 10^5$ cpm/ml in Tris-HCl buffered saline pH 8.2, containing 0.05% Tween-20+5% FBS, for 1 hour at room temperature. Finally, strips were washed in T-PBS +1% FBS and dried.

In immunoprecipitation experiments, gels were stained with Coomassie blue to identify the position of molecular weight (M.W.) markers. The M.W. of antigens on Western blots were determined by comparison with transferred pre-stained standards (BRL, Gaithersburg, MD). Dried nitrocellulose strips or gels were autoradiographed using X-Omat AR Plus film (Eastman-Kodak, Rochester, NY) at −70° C.

Immunization by Various Routes of Antigen Presentation

Figure 1:
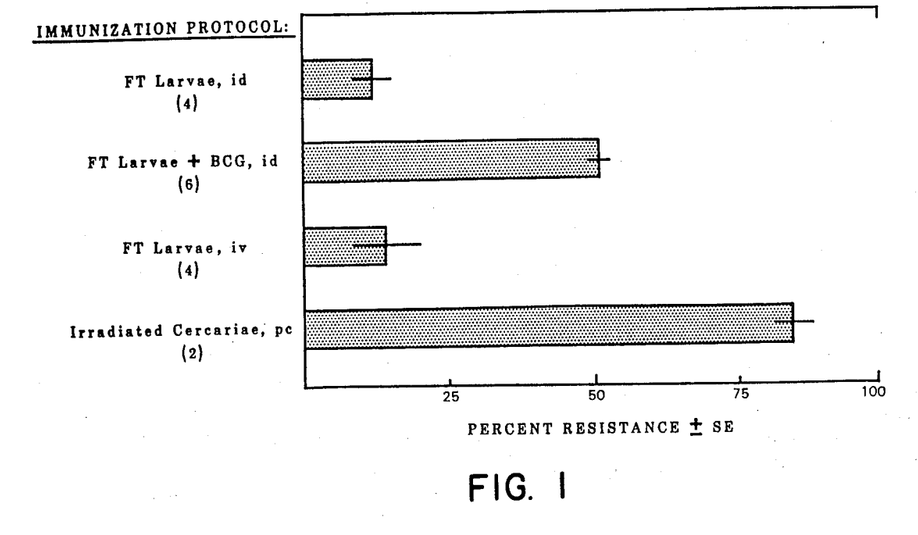

Intradermal (id) injection of dead larvae alone resulted in little resistance to challenge S. mansoni infection (FIG. 1). However, when the dead parasites were mixed with a bacterial adjuvant prior to id inoculation, highly significant protection against challenge infection was achieved. In seven tests, mice immunized by id injection of larvae plus Mycobacterium bovis, strain BCG, demonstrated 44 to 69% fewer adult worms developing from the infecting cercariae than did mice receiving saline only (p <0.0001 in each case). Thus, protection induced by intradermal immunization with dead larvae plus BCG was roughly 60% of the level achieved by percutaneous vaccination with living radiation-attenuated cercariae in these experiments. In contrast, intravenous (IV) injection of equal numbers of dead larvae conferred no resistance to challenge infection. Intravenous injection of dead parasites in conjunction with BCG was not attempted, since IV administration of BCG alone has been reported to render mice non-specifically resistant to subsequent S. mansoni infection(Civil et al, J. Inf. Dis. 137: 550, 1978).

Specificity of id Immunization with FT Larvae and BCG

In agreement with the observations of Civil et al, supra, cutaneous inoculation with BCG alone did not produce resistance (Table 1). Moreover, significant resistance was achieved using heat-killed BCG or 10-fold lower concentrations of living BCG in association with dead larvae. Therefore, BCG appeared to be acting as a potent adjuvant in association with larval antigens under conditions in which it is not protective when administered alone.

TABLE 1

| BCG functions as an adjuvant for immunization against S. mansoni | |
|---|---|
| Immunization Protocol[a] | % Resistance Conferred[b] |
| Control (saline, id) [6] | — |
| FT larvae + $5 \times 10^6$ CFU BCG, id [6] | $51 \pm 2^c$ |
| $5 \times 10^6$ CFU BCG only, id [6] | $8 \pm 2$ |
| FT larvae + heat-killed BCG, id [1] | $54^c$ |
| FT larvae + $5 \times 10^5$ CFU BCG, id [1] | $44^d$ |

[a]C57BL/6J mice were treated by id injection of phosphate-buffered saline only (control) or saline containing schistosomula of S. mansoni that had been killed by one cycle of freezing at −20° C. and thawing. Mycobacterium bovis, strain BCG, Phipps substrain, was included at $5 \times 10^6$ or $5 \times 10^5$ colony-forming units (CFU). BCG was heat-killed by boiling for 30 minutes, followed by two cycles of freezing and thawing FT and used at the equivalent of $5 \times 10^6$ CFU.
[b]Animals were infected with 150 to 200 S. mansoni cercariae at 4 weeks after immunization. Values in brackets indicate the number of experiments performed. Results are expressed as mean percent resistance ± standard error (SE).
[c]designates a significant reduction in numbers of worms recovered from immunized mice at the 99.9% level in each individual experiment, calculated by the Student's t test.
[d]designates significance at the 99.5% level.

Correlation of Resistance with Specific Immune Responses

Immune responses against schistosome antigens were followed in immunized mice by skin testing with soluble worm antigens and by determining levels of circulating antibodies against tegumental and soluble antigens at the time of challenge infection (Table 2). Mice vaccinated with highly irradiated cercariae were again utilized as positive controls. It was observed that these animals were highly resistant to S. mansoni infection and showed strong immediate and delayed hypersensitivity (IH,DH) to soluble antigens as well as significant levels of antibodies to larval surface antigens. Likewise, animals immunized by id injection of dead larvae plus adjuvant were significantly resistant to infection and demonstrated strong specific DH to SWAP. Similar DH reactivity was observed against larval antigens in these mice. However, these animals showed only low levels of circulating antibody to surface antigens.

TABLE 2

| Immunization against S. mansoni: Correlation between resistance and other immune parameters | | | | | | |
|---|---|---|---|---|---|---|
| | % Resistance | Skin-test responses to SWAP[b] | | Humoral Responses | | |
| Immunization Protocol[a] | Conferred | IH | DH | Surface antigens[c] | SLAP[d] | SWAP[d] |
| Control (saline, id) | — | 16 ± 6 | 4 ± 4 | 14 ± 3 | 0.15 ± 0.12 | 0.17 ± 0.13 |
| Attenuated cercariae | 85 ± 5 | 44 ± 9 | 24 ± 5 | 189 ± 26 | 0.81 ± 0.16 | 0.94 ± 0.19 |
| FT larvae | 51 ± 2 | 29 ± 7 | 29 ± 4 | 88 ± 21 | 0.64 ± 0.24[e] | 1.26 ± 0.39[f] |

TABLE 2-continued

Immunization against *S. mansoni*: Correlation between resistance and other immune parameters

| Immunization Protocol[a] | % Resistance Conferred | Skin-test responses to SWAP[b] | | Humoral Responses | | |
|---|---|---|---|---|---|---|
| | | IH | DH | Surface antigens[c] | SLAP[d] | SWAP[d] |
| plus BCG, id | | | | | | |
| FT larvae, iv | 14 ± 6 | 28 ± 11 | 3 ± 3 | 234 ± 70 | 0.95 ± 0.13[e] | 0.63 ± 0.22[f] |
| BCG only, id | 8 ± 2 | 28 ± 13 | 7 ± 6 | 11 ± 2 | 0.07 ± 0.10 | 0.08 ± 0.04 |

[a]Mice were immunized as described previously. Resistance is expressed as mean percent ± SE for 2 to 6 experiments, as shown in FIG. 1. All immune parameters were measured at the time of challenge infection, 4 weeks after immunization.
[b]Skin testing was performed in the footpads using 100 μg protein of soluble worm antigens. Numbers represent the means of differences in thickness between the footpad receiving antigen and the footpad receiving an equivalent volume of saline (mean value in mm × $10^{-2}$ ± SD for every experiment performed) at 30 minutes (immediate hypersensitivity, IH) or 24 hours (delayed hypersensitivity, DH) after antigen injection.
[c]Serum antibody levels to larval surface antigens were measured by indirect immunofluorescence using the experimental sera as first antibody and a goat anti-mouse IgG antisera recognizing both IgM and IgG as second antibody, with living schistosomula as antigen. Fluorescence was quantitated using a photometer; values are expressed as mean in relative fluorescence units ± SD for al experiments.
[d]Antibody levels to soluble larval (SLAP) and adult worm antigens (SWAP) were measured by ELISA using a 1:10 dilution of experimental sera and a second antibody against mouse IgG heavy and light chains. Values are expressed as mean O.D. units at 410 nm ± SD for all experiments.
[e]ELISA titers were calculated as the last dilution giving an O.D. reading greater than 3 S.D. from the mean value of control sera, Anti-SLAP titers of sera from id-immunized and iv-injected mice were both 1:200.
[f]Anti-SWAP titers were 1:400 and 1:100 for sera from id-immunized and iv-injected mice, respectively.

Mice given dead larvae IV were not resistant and failed to demonstrate DH, although they developed higher levels of circulating anti-tegumental antibodies, equivalent to those found in mice vaccinated with irradiated living larvae. Similarly, when specific IgG and IgM antibodies in sera from these mice were measured separately, the levels were equivalent to those in sera from mice vaccinated with irradiated cercariae. Thus, by indirect immunofluorescence using a second antibody specific for mouse IgG, sera from mice injected IV with FT larvae gave a mean photometric determination of 36±8 RFU while sera from vaccinated mice registered 37±14 RFU. Similarly, with second antibody recognizing only IgM, specific fluorescence determinations of 166±30 RFU and 100±23 RFU were achieved by the two sera, respectively. Furthermore, when antibodies were measured at one week after challenge infection to account for anamnestic response, levels in all groups had approximately doubled with those in id immunized animals remaining proportionally half of those in IV inoculated or vaccinated mice. It is clear from these results that production of high levels of circulating IgG and IgM antibodies to larval tegumental antigens is not in itself sufficient to confer resistance.

Induction of circulating antibodies against water soluble components of schistosomula and adult worms was also analyzed in animals immunized with FT larvae. Mice vaccinated with irradiated cercariae or injected with FT larvae IV, or id in conjunction with BCG, all developed significant levels of anti-SLAP antibodies (titer 1:200 AS). However, the id-immunized animals consistently had slightly higher levels of anti-SWAP antibodies both in terms of binding intensity at a 1:10 dilution (Table 2) and antibody titer (1:400 vs 1:100 with sera from IV-injected mice).

Protective Parasite Immunogens are Present in Soluble Fractions of Schistosomulum Lysates.

Original studies employed newly transformed schistosomula that had been killed by one cycle of freezing and thawing as immunogen. The larval lysate contained both soluble and particulate (membrane) components of the parasites. Since immune response against larval membrane is believed to be a major mechanism of resistance against schistosomiasis, it was of interest to determine whether the immunogenic determinants in this preparation were membrane-associated. FT larvae were, therefore, separated into soluble and particulate fractions. Concentrated, frozen larvae were resuspended in PBS and centrifuged at 12,000×G for 5 minutes. Supernatant fluid (supernate) was used directly to immunize in conjunction with BCG. Insoluble material (pellet) was washed 3 times in PBS, resuspended to the original volume, and used for immunization with BCG. Alternatively, FT schistosomula were adjusted to the same concentration, sonicated, and then subjected to high speed centrifugation and the aqueous fraction (SCHLAP) was used for immunization. It was observed that total FT-larval lysate administered id with BCG consistently resulted in highly significant levels of resistance to challenge infection (Table 3). In contrast at equivalent concentrations, pelleted membrane material was relatively less immunogenic. Interestingly, however, parasite immunogens were also present in the aqueous fraction remaining after low-speed or ultracentrifugation (31-47% resistance, Table 3). In a total of 5 tests utilizing SCHLAP as antigen, a mean of 48% protection (±9, S.D.) was observed, indicating that soluble schistosomulum components are highly immunogenic in conjunction with BCG.

TABLE 3

Protective immunogens are present in soluble as well as particulate fractions of FT-schistosomulum lysates

| Exp. No. | Antigen[a] | Number of adult worms recovered from:[b] | | % Protection[c] | P value[d] |
|---|---|---|---|---|---|
| | | Control mice | Immunized mice | | |
| 1 | Total Lysate | 57 ± 18 (10) | 28 ± 5 (10) | 51% | <0.001 |
| | Pellet | | 34 ± 14 (8) | 40% | <0.02 |
| | Supernate | | 30 ± 15 (6) | 47% | <0.05 |
| 2 | Total Lysate | 71 ± 20 (10) | 42 ± 11 (10) | 41% | <0.001 |
| | Pellet | | 46 ± 14 (10) | 35% | <0.005 |
| | Supernate | | 49 ± 20 (11) | 31% | <0.02 |
| 3 | Total Lysate | 61 ± 12 (9) | 36 ± 13 (10) | 42% | <0.001 |
| | Pellet | | 50 ± 10 (10) | 19% | <0.05 |
| | SCHLAP | | 34 ± 13 (11) | 45% | <0.001 |
| 4 | Total Lysate | 62 ± 15 (9) | 32 ± 22 (10) | 48% | <0.001 |

TABLE 3-continued

Protective immunogens are present in soluble as well as particulate fractions of FT-schistosomulum lysates

| Exp. No. | Antigen[a] | Number of adult worms recovered from:[b] | | % Protection[c] | P value[d] |
|---|---|---|---|---|---|
| | | Control mice | Immunized mice | | |
| | SCHLAP | | 37 ± 25 (7) | 41% | <0.05 |

[a]Larval antigens were prepared as described in Materials and Methods. Mice were immunized with 0.1 ml of antigen combined with 5 × 10[6] CFU of BCG administered intradermally/subcutaneously.
[b]Control mice were injected with saline only. All animals were infected with 150 to 200 cercariae at 4 weeks after immunization. Adult worms were recovered 6 weeks after infection by portal perfusion. Numbers represent the mean recovery ± standard deviation for the number of mice shown in parenthesis.
[c]Percent protection was determined as 1 - (the mean number of worms recovered from immunized mice divided by the number recovered from controls). Mice injected with BCG only gave protection values of from 0 to 17% in these experiments.
[d]Significance was determined by the Students t test.

Protective Parasite Antigens are not Stage Specific.

Newly transformed schistosomula were originally chosen for immunization studies because this stage of the parasite is believed to be a major target of protective immune response. However, it was of interest to determine whether protective antigens were present in other stages of the parasite as well. An initial test employing equivalent numbers of FT-cercariae, in which 63% protection was obtained (Table 4), revealed that the infective stage of the parasite was also immunogenic and suggested that protective determinants were present prior to transformation to the physiologically adapted form.

Due to size and complexity of adult schistosomes, it was impossible to inject a FT lysate of adult worms id. Moreover, the size differential between larval and adult forms (approximately 100-fold increase in length) made quantitative comparisons on the basis of number of organisms unfeasible. Therefore, a soluble preparation analogous to SCHLAP was produced by ultracentrifugation of homogenized adult worms (SWAP), and standardized according to protein content.

TABLE 4

Protective immunogens are present in cercariae and adult worms as well as newly transformed schistosomula

| Exp. No. | Antigen[a] | Number of adult worms recovered from: | | % Protection | P value |
|---|---|---|---|---|---|
| | | Control mice | Immunized mice | | |
| 1 | FT-schistosomula (10[4]) | 48 ± 11 (9) | 15 ± 13 (8) | 68% | <0.001 |
| | FT-cercariae (10[4]) | | 17 ± 10 (9) | 63% | <0.001 |
| 2 | FT-schistosomula (10[4]) | 55 ± 14 (8) | 35 ± 12 (8) | 36% | <0.01 |
| | SWAP (0.1 mg) | | 44 ± 22 (8) | 20% | N.S. |
| | SWAP (1.0 mg) | | 16 ± 11 (7) | 70% | <0.001 |
| 3 | FT-schistosomula (10[4]) | 93 ± 15 (6) | 52 ± 19 (7) | 44% | <0.005 |
| | SWAP (1.0 mg) | | 56 ± 11 (8) | 40% | <0.001 |

[a]Mice were injected with parasite lysate containing 10[4] organisms/0.1 ml or with soluble antigens antitated according to protein content (0.1 or 1.0 mg/0.1 ml) combined with BCG.
N.S. = not statistically significant at the 95% confidence limit.

adult worms (SWAP), and standardized according to Whereas immunization with 0.1 mg of SWAP was not significantly protective, immunization with 10-fold higher concentrations produced strong resistance to challenge infection (Table 4). These preparations contained approximately 5 times the protein concentration of SCHLAP required for induction of immunity, suggesting that while protective determinants are present in adult worms they represent a smaller proportion of the overall protein content of the organisms than in schistosomula.

Figure 2:
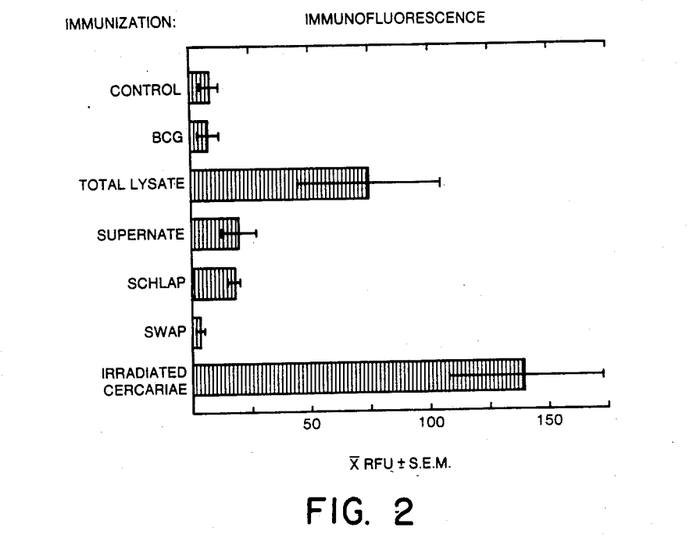
FIG. 2 shows indirect immunofluorescence assay of antibodies against schistosomulum surface antigens in sera from immunized mice. Sera was obtained from C57BL/6J mice 4 weeks after immunization with FT-larval lysate or soluble larval (supernate, SCHLAP) and adult worm (SWAP) antigens plus BCG, or with 500 50Kr irradiated cercariae. Negative control sera were obtained from normal C57BL/6 mice and mice injected 4 weeks previously with BCG alone. Living 3 hour schistosomula were reacted with control or immune sera at a 1:2 dilution, washed and reacted with a fluorescein- conjugated second antibody recognizing mouse IgM, IgA and IgA. Intensity of fluorescence was quantitated photometrically and expressed in mean relative fluorescence units. Results are presented as the mean of 3 to 5 experiments=S.E.M.

Humoral Reactivity Toward Larval Surface Antigens in Mice Immunized with Soluble Schistosome Antigens:

Since soluble antigens can be more easily purified than membrane-associated antigens, efforts were concentrated on characterization of immune reactivity in animals protected by exposure to soluble antigens. Immunized mice were bled at a time of challenge infection and the sera were initially analyzed for reactivity against schistosomulum surface antigens by indirect immunofluorescence (FIG. 2). It was observed that injection of BCG alone did not result in protection against infection (0 to 7% in these tests with respect to unimmunized controls) and failed to stimulate production of antibodies against tegumental antigens. Immunization with total FT-larval lysate induced production of antibodies against tegumental antigen; nevertheless, the level of anti-surface antigen reactivity was low compared to that in sera from mice immunized with irradiated cercariae (FIG. 2).

Immunization with pelleted membrane material stimulated anti-tegumental antibody production at levels equivalent to that in sera from mice vaccinated with total lysate. However, immunization with the three soluble preparation (FT-larval supernate, SCHLAP and SWAP) failed to stimulate production of significant levels of antibodies to tegumental antigens as detected by surface immunofluorescence. To explore the possibility that immunization with SWAP plus BCG might elicit responses against membrane antigens of older worms, indirect immunofluorescence assays were also performed using 2 week and 6 week old liver stage worms as targets. When used at a 1:2 dilution, sera from SWAP-immunized mice gave fluorescence values of 15 to 7 RFU, respectively, against 2 week and 6 week worms. These values were not significantly greater than those achieved by control sera under the same conditions (10 and 5 RFU, respectively).

Figure 3:
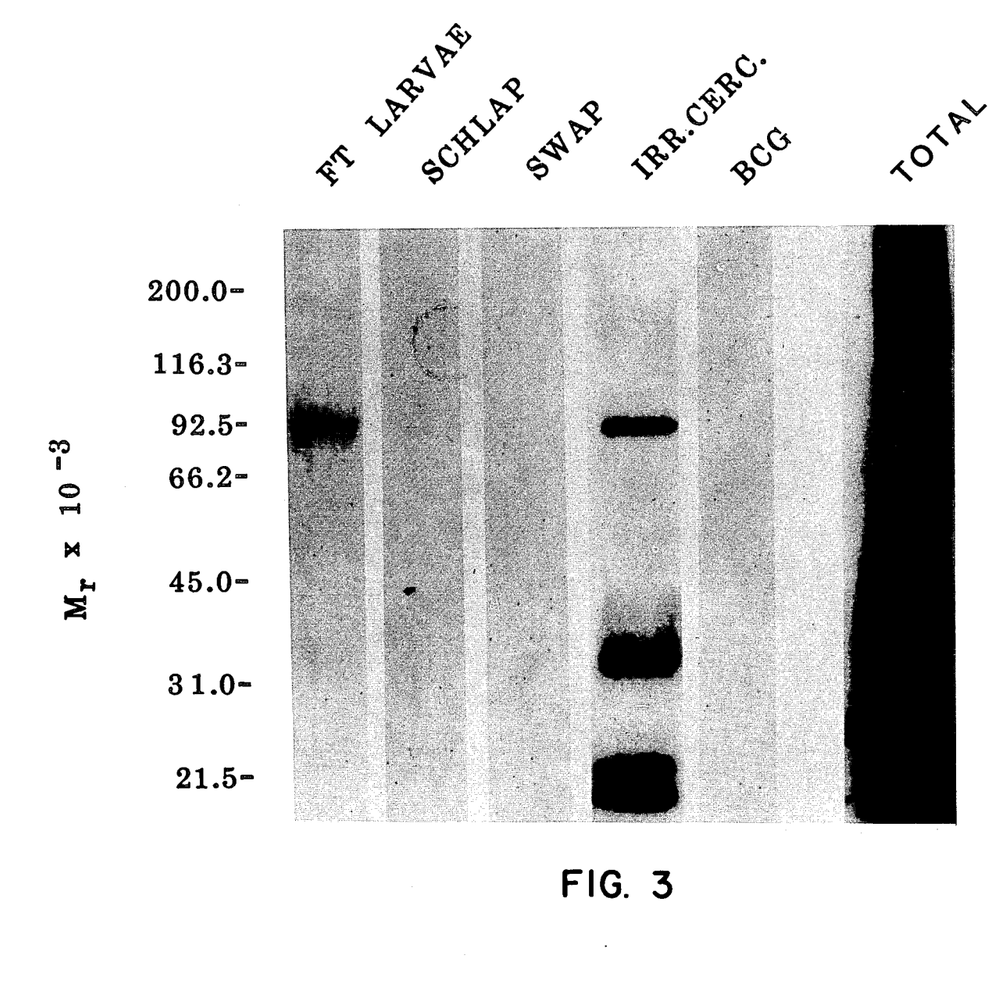
FIG. 3 shows autoradiograph of SDS-PAGE of $^{125}$I-labelled surface antigens of 3 hour schistosomula after immunoprecipitation with sera from mice immunized with FT larvae plus BCG, SCHLAP plus BCG, SWAP plus BCG, or irradiated cercariae. Control sera was obtained from mice exposed to BCG alone.

These observations were confirmed by immunoprecipitation of $^{125}$I-labelled surface antigens and SDS-PAGE (FIG. 3). Whereas sera from irradiated cercariae-vaccinated mice recognized multiple tegumental antigens, sera from mice immunized with FT larvae precipitated only one major surface antigen with a relative molecular weight ($M_r$) of $94 \times 10^3$. Moreover, sera from mice immunized with soluble antigens failed to precipitate any detectable iodinated surface components of newly transformed schistosomula, again indicating a lack of anti-tegumental reactivity in these animals at the time of challenge.

Figure 4:
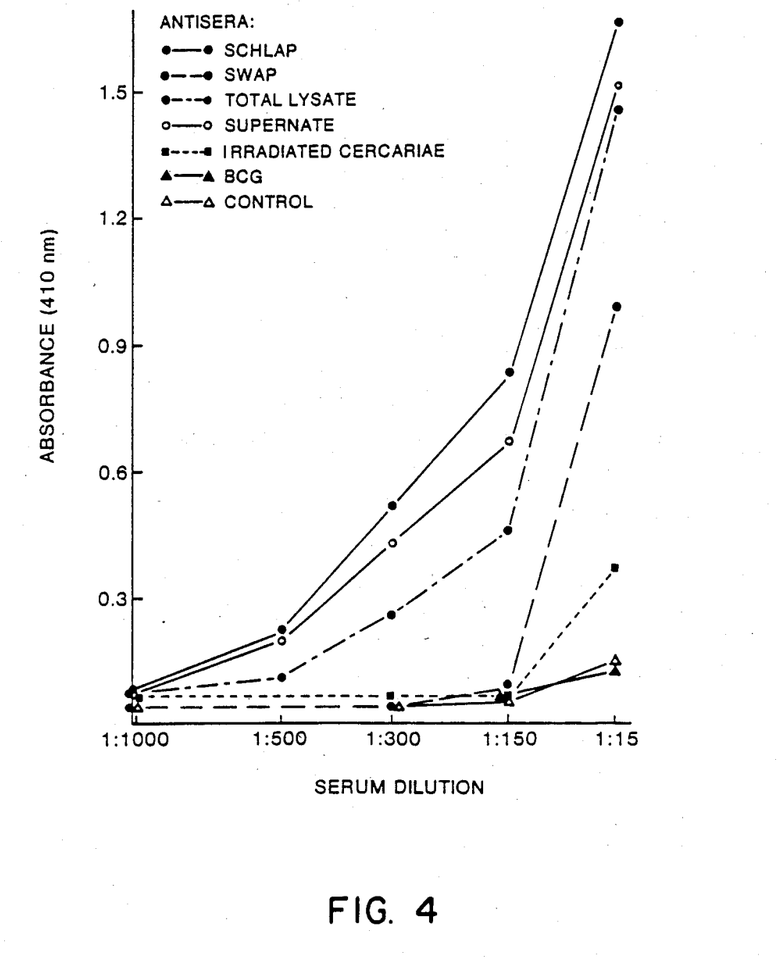
FIG. 4 shows enzyme-linked immunosorbent assay of antibodies against SWAP in sera from immunized mice. Sera taken 4 weeks after immunization was reacted at dilutions of 1:15 to 1:1000 with SWAP (10 ug/ml) in microtiter wells. Peroxidase-conjugated anti-mouse Ig was utilized as second antibody. Optical density was measured at 410 nm and presented as the mean of quadruplicate samples.

Humoral Reactivity Toward Soluble Antigens in Mice Immunized with Soluble Schistosome Antigens The same sera were also analyzed for recognition of soluble adult and larval antigens by ELISA. It was observed that sera from unimmunized control mice and mice injected with BCG only did not bind to SWAP in the ELISA assay, even at high concentrations (FIG. 4). Sera from mice immunized with total larval lysate showed strong anti-SWAP activity, both in terms of initial binding intensity at high concentration and titer. Immunization with pelleted membrane material also elicited positive anti-SWAP response, although levels of reactivity were variable between experiments. Immunization with soluble schistosomulum (supernate, SCHLAP) and adult worm (SWAP) antigens resulted in strong anti-SWAP antibody reactivity, although titers were higher in animals exposed to larval antigens (FIG. 4).

Antibody response to SCHLAP followed the same pattern, although binding was much weaker even at high serum concentrations. Thus, sera from mice immunized with FT larvae reacted with SCHLAP with an absorbance of 0.24 at a 1:15 dilution, while at the same concentration sera from mice immunized with supernate, SCHLAP or SWAP gave absorbances of 0.23, 0.30 and 0.16, respectively. For comparison, sera from irradiated cercariae-vaccinated mice yielded an absorbance of 0.31 in the same assay, while at the same concentration sera from BCG-injected animals showed binding of only 0.06 O.D. units. All immune sera had anti-SCHLAP titers of 1:150.

Figure 5:
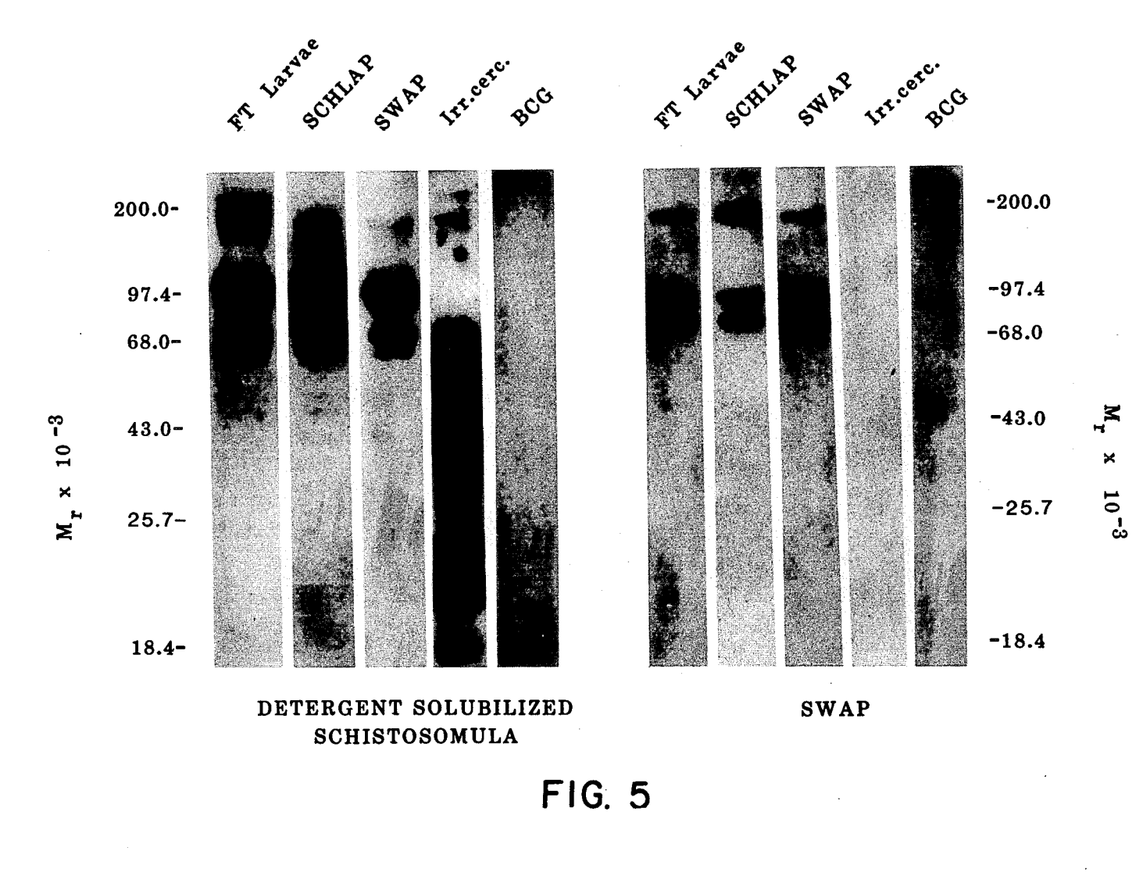
FIG. 5 shows Western blot analysis of the reactivity of serum from mice immunized with FT larvae plus BCG, SCHLAP plus BCG, SWAP plus BCG or irradiated cercariae against SDS-PAGE separated antigens of detergent-solubilized schistosomula and SWAP. Control sera was obtained from mice injected with BCG only.

Western blot analysis of sera from immunized mice showed protected animals to recognize a limited number of antigens of high molecular weight in SWAP and total detergent-solubilized larval preparations. The adult worm antigens were of M approximately 188, 95 and $78 \times 10$ (FIG. 5) Sera from mice immunized with FT larvae, SCHLAP or SWAP plus BCG recognize larval antigens with $M_r$ of 200-14 188, 104, 98, 71 and $64 \times 10$. Interestingly, sera from irradiated-cercariae-immunized animals failed to react with the two major larval antigens of $M_r$ 104 and $93 \times 10$, although several components of lower $M_r$ were recognized. In agreement with previous ELISA results (FIG. 4), sera from mice vaccinated with attenuated cercariae also showed little reactivity against SWAP.

It is quite evident from the above that a dependable and highly effective immunization procedure against *S. Mansoni* using nonliving parasite antigens (SWAP OR SCHLAP) in a soluble form as disclosed herein is now possible. The purified and method also provides a new model for the study of specific effector mechanisms of resistance and for the chemical definition of a vaccine against schistosome parasites.

It has also been discovered that the route of administration of antigen is quite critical in eliciting immunity in the host. Furthermore, it has been shown that the immunity induced by this procedure is accompanied by strong antigen-specific DTH, but that humoral responses against the tegument of the parasite are not essential for protection.

A vaccine or pharmaceutical composition or preparation for controlling or preventing schistosomiasis or *S. mansoni* induced disease comprising isolated, soluble antigen or fractions thereof in accordance with the present invention and a pharmaceutically acceptable carrier is, of course, now possible from the present disclosure. The carrier or medium in which the vaccine is prepared should, of course, be non-toxic and free of undesirable germs or microorganisms and the like. Such carrier can be any suitable sterile medium, a solid or a liquid e.g., physiological saline, and the like. The composition, of course, should also be fortified with a suitable adjuvant, such as BCG or other adjuvants which induce cell-mediated immunity.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of inducing protective immunity against *Schistosoma mansoni* parasitic infection in a host comprising intradermally administering to said host an immunogenic amount of isolated, membrane-free, soluble parasite fraction and a bacterial adjuvant selected from the group consisting of *Myovacterium bovis*, strain bacille Calmette Guerin and *Bordetella pertussis*.

2. A pharmaceutical composition for controlling or preventing Schistosomiasis in mammals comprising a composition of an immunogenic amount of an isolated, membrane-free, soluble parasite-fraction and a bacterial adjuvant selected from the group consisting of *Myobacterium bovis*, strain bacille Calmette Guerin and *Bordetella pertussis* in a pharmaceutically acceptable carrier, said composition inducing immunity against *Schistosoma mansoni* parasitic infection when administered intradermally to a host infected with said infection.

3. The composition of claim 2 being a vaccine in a sterile carrier.

* * * * *